US007481814B1

(12) United States Patent
Metzger

(10) Patent No.: US 7,481,814 B1
(45) Date of Patent: Jan. 27, 2009

(54) METHOD AND APPARATUS FOR USE OF A MILL OR REAMER

(75) Inventor: Robert Metzger, Wakarusa, IN (US)

(73) Assignee: Biomet Manufacturing Corporation, Warsaw, IN (US)

( * ) Notice: Subject to any disclaimer, the term of this patent is extended or adjusted under 35 U.S.C. 154(b) by 287 days.

(21) Appl. No.: 10/628,816

(22) Filed: Jul. 28, 2003

(51) Int. Cl.
 *A61F 5/00* (2006.01)
(52) U.S. Cl. ....................................................... 606/87
(58) Field of Classification Search ............. 606/79, 606/80, 86, 87, 62, 170, 88, 89, 86 R
See application file for complete search history.

(56) References Cited

U.S. PATENT DOCUMENTS

| 4,952,213 A | * | 8/1990 | Bowman et al. ............... 606/79 |
| 5,047,032 A | | 9/1991 | Jellicoe |
| 5,171,244 A | | 12/1992 | Caspari et al. |
| 5,228,459 A | | 7/1993 | Caspari et al. |
| 5,263,498 A | | 11/1993 | Caspari et al. |
| 5,304,181 A | | 4/1994 | Caspari et al. |
| 5,312,411 A | | 5/1994 | Steele et al. |
| 5,409,489 A | * | 4/1995 | Sioufi ............................ 606/80 |
| 5,468,243 A | | 11/1995 | Halpern |
| 5,486,180 A | | 1/1996 | Dietz et al. |
| 5,534,005 A | | 7/1996 | Tokish, Jr. et al. |
| 5,540,694 A | * | 7/1996 | DeCarlo et al. ............... 606/80 |
| 5,556,399 A | * | 9/1996 | Huebner ....................... 606/80 |
| 5,616,146 A | | 4/1997 | Murray |
| 5,643,272 A | | 7/1997 | Haines et al. |
| 5,676,668 A | | 10/1997 | McCue et al. |
| 5,681,316 A | | 10/1997 | DeOrio et al. |
| 5,690,636 A | | 11/1997 | Wildgoose et al. |
| 5,788,701 A | | 8/1998 | McCue |
| 5,908,424 A | | 6/1999 | Bertin et al. |
| 5,976,145 A | | 11/1999 | Kennefick, III |
| 6,063,091 A | | 5/2000 | Lombardo et al. |
| 6,228,091 B1 | | 5/2001 | Lombardo et al. |
| 6,482,209 B1 | | 11/2002 | Engh et al. |
| 6,551,324 B2 | | 4/2003 | Muller |
| 7,255,702 B2 | * | 8/2007 | Serra et al. ..................... 606/80 |
| 2004/0102785 A1 | | 5/2004 | Hodorek et al. |

* cited by examiner

*Primary Examiner*—Eduardo C Robert
*Assistant Examiner*—James L Swiger, III
(74) *Attorney, Agent, or Firm*—Harness, Dickey & Pierce, P.L.C.

(57) ABSTRACT

An assembly and method for providing a less invasive resection of various bone portions. Generally, the assembly includes a positioning rod and a reamer that may be moved relative to the positioning rod with a guiding portion. The method allows for use of the assembly through a substantially small incision to reduce trauma to the patient during the resection procedure and decrease recovery time.

25 Claims, 4 Drawing Sheets

METHOD AND APPARATUS FOR USE OF A MILL OR REAMER

FIELD

The present disclosure relates generally to an apparatus and method for orthopedic surgery, and particularly to a method and apparatus for a less or minimally invasive distal femoral resection.

BACKGROUND

In the human anatomy, various bone portions articulate at joints relative to another bone portion. For example a femur, in the human anatomy, articulates relative to a tibia to form the knee joint.

Although a natural or normal anatomy generally allows for substantially smooth articulation of various portions, circumstances, such as, injury or age, may reduce the pain free and easy articulation of the various bone portions. Therefore, procedures, such as orthopedic procedures, may be performed to substantially repair and make more pain free articulations of the various anatomical portions.

Also, various other anatomical portions, such as other bone sections, may become weakened and need repair over time. Therefore, other procedures, such as, resection or removal of selected portions of the bone portion may be required. The resection generally prepares the bone portion for receiving a selected implant to allow for replacement or healing of the selected or injured bone portion. To repair a joint, such as a knee joint, resection of the various femoral and tibial portions may be required. The portions are resected to receive a distal femoral implant to replace the condyles of the femur.

Generally, the resection of the bone portions may cause injury to soft tissue to access the bone portions. For example, the soft tissue may be pierced or cut to gain access to the bone portion which is underneath the soft tissue. Therefore, the soft tissue may be cut and moved to allow access to the selected bone portion which may cause some injury to the soft tissue. In addition, the tools necessary to resect the various portions are generally large in size and require the large openings.

Therefore, it is desired to provide a procedure which allows for substantially small incisions to perform the necessary procedures. It is further desired to provide surgical elements which allow for minimally or less invasive procedures and minimal trauma during a surgical procedure.

SUMMARY

An apparatus for providing a less or minimally invasive resection of a selected bone portion. For example, providing an apparatus for a less invasive resection of a distal femoral bone portion for resection to allow a distal femoral implant. Generally, resection of the distal section of the condyles of the femur is performed to receive a portion of a knee implant. Although the various instruments may be used for resection of various other bone portions, resecting a distal femoral portion is merely exemplary.

Also, a method for performing a minimally or less invasive procedure of a selected bone portion, such as distal femoral resection for a knee replacement. The resection being performed through a substantially minimally or less invasive incision through the dermis and other soft tissues to minimize trauma to the patient. Although the various techniques may be used in any other appropriate minimally invasive procedure for resecting a selected portion of the bone.

According to a first embodiment is an assembly to resect a selected bone portion. The assembly includes a positioning member fixed relative to the selected bone portion. A guiding member rotatably extends from the positioning member. Also, a resecting member is guided by the guiding member. The resecting member is rotatable around the positioning member to at least one position relative to the positioning member.

According to a second embodiment a resection assembly allows resection of a selected bone portion. The assembly includes a positioning rod disposed within the selected bone portion through an incision formed relative to the selected bone portion. A first guiding member is moveable relative to the positioning rod. A resecting tool extends along an axis and is guided by the guiding member such that a selected portion of the selected bone portion is resected at a selected time. A second guiding assembly is between the first guiding member and the resecting tool to select an axial movement of the resecting tool. The positioning rod and the resecting tool are passed through the incision.

According to a third embodiment is a method to resect a selected bone portion with a resecting assembly that includes a resecting tool is guideable relative to a positioning member fixed relative to the selected bone portion. The method includes forming an incision in a soft tissue relative to the selected bone portion. A positioning member is passed through the formed incision and is fixed relative to the selected bone portion through the formed incision. The resecting tool is passed through the formed incision and moved about the positioning member. A selected portion of the selected bone portion is resected to form a resected bone portion.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF VARIOUS EMBODIMENTS

The following description of various embodiments is merely exemplary in nature and is in no way intended to limit the invention, its application, or uses. Although the following description relates generally to resection of a distal femoral portion, such as a condyle on the distal end of the femur, it will be understood that the apparatus and method may be used for other appropriate resections. For example, the apparatus may be used for resection of proximal femoral or tibial portions and other various or appropriate bone portions. Also, the methods described herein, are merely exemplary of the method of use of the apparatus and not intended to limit the scope thereof. Therefore, it will be understood that the following description is merely exemplary of the method and apparatus and not intended to be a limiting description.

Figure 1:
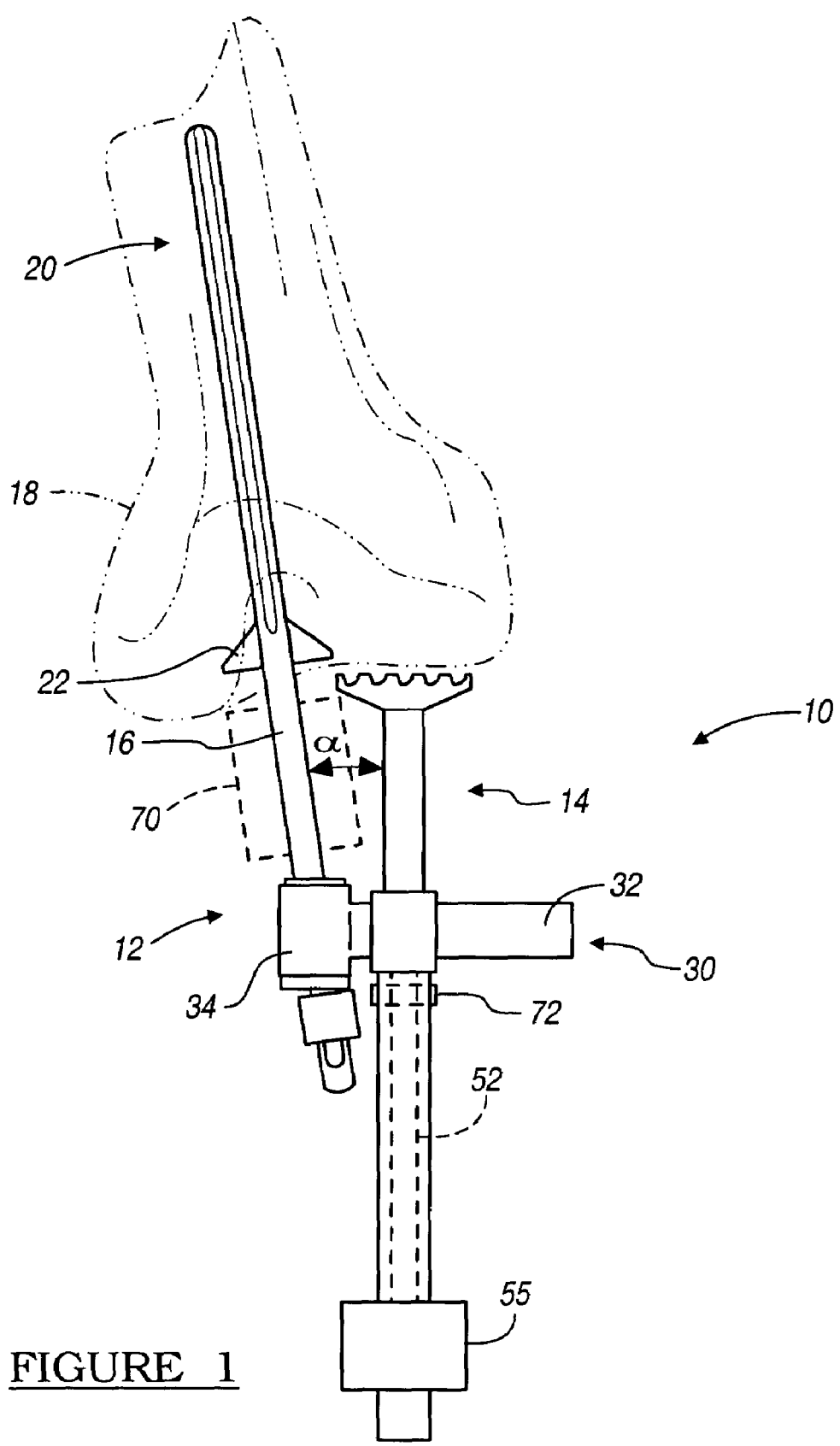
FIG. 1 is a plan view of a resecting assembly according to an embodiment.

With reference to FIG. 1, an orthopedic instrument assembly 10 is illustrated. The assembly 10 generally includes a reamer guiding portion 12 and a reamer 14. The reamer 14 may be provided integrally with the reamer guide portion 12 or may be provided separately therefrom.

The reamer guide portion 12 generally includes a fixation or positioning rod 16 that can be positioned into a bone, shown in phantom 18. The positioning rod 16 may be positioned in a medulla portion of the bone 18, but may not be necessarily so positioned. In addition, the positioning rod 16 need not necessarily be positioned within any portion of the bone 18. For example, the positioning rod 16 may be otherwise fixed to the bone 18 to guide the reamer 14. Nevertheless, the positioning rod 16 generally includes a distal bone engaging portion 20 that defines a holding structure or fin 22 to limit rotation of the rod 16. Therefore, the rod 16 can be fit in the bone 18 and be substantially limited in rotation relative to the bone 18.

Extending from the fixation of the positioning rod 16 is a movable or rotatable arm 30. The rotatable arm 30 is rotatable about the positioning arm 16 such that the reamer 14 may rotate about the positioning rod 16. The rotatable arm 30 generally includes an arm portion 32 and a collar member 34. A proximal portion 24 of the positioning rod 16 extends through the collar portion 34 of the rotatable member 30. An appropriate locking member 36, such as a nut, is used to fix the rotatable member 30 relative to the positioning rod 16. Also an appropriate bushing 38 may be provided to allow for selected articulation and rotation between the rotatable arm 30 and the positioning arm 16.

As illustrated in FIG. 1, the positioning rod 16 may be provided at an angle α relative to the reamer. This can allow for substantial alignment and ease of movement of the reamer 14 relative to the positioning rod 16. Although the angle α may differ depending upon the bone portion to be resected or the patient at which the procedure occurs, it will be understood that any appropriate angle α may be used. Also, the bushing 38 may be a compression bushing such that a force applied to it, such as with the locking nut 36, compresses the bushing 38 to substantially fix the rotating member 30 relative to the positioning rod 16.

The movable arm 32 operably engages a reamer holding portion 40. The reamer holding portion 40 defines a bore 42 to operably engage the rotatable arm 32 during operation. The reamer engaging portion 40 also defines a reamer bore 44 that operably engages the reamer 14. Therefore, the reamer 14 may pass through the reamer engaging bore 44 such that the reamer 14 may rotate within the reamer engaging bore 44.

The reamer 14 generally includes a reamer head or reaming head 50. The reaming head 50 may be any appropriate dimension, but is generally about 0.5 cm to about 4.0 cm. The reaming head 50 extends distally from a shaft 52 that terminates in a proximal tool engaging portion 54. The shaft 52 may also be any appropriate dimension, but is generally about 0.25 cm to about 4.0 corm. The shaft 52 translates rotational movement from a tool or manual operation to the head 50. The reamer 14 is held in place with the reamer engaging member 40 relative to the positioning rod 16.

Affixed relative to the tool engaging end 54 of the reamer 14 is a spacer or depth guide 55. The depth guide 55 is generally threadably engaged to the shaft 52 of the reamer 14. This allows the depth guide 55 to include a selective axial position relative to the shaft 52 of the reamer 14. Simply, the depth guide 55 can be moved by rotating the depth guide 55 relative to the reamer shaft 52. Extending along a portion of the reamer shaft 52 is a sleeve 56. The sleeve 56 is generally between the depth guide 55 and the reamer engaging member 40. In this way, the translation of the reamer 14 is limited by engagement between the reamer engaging portion 40, the sleeve 56, and the depth guide 55. The depth to which the reamer 14 may pass is selected by rotating the depth guide 55 to engage the sleeve 56 at an appropriate time. Therefore, the reamer 14 may be pulled proximally and a selected spacer or measurement tool is used to select a depth for movement of the reamer 14. The depth guide 55 is moved to the selected position to allow only the selected depth. In this way, reaming the bone 18 may be selected by positioning the depth guide 55 on the shaft 52 relative to the sleeve 56.

Figure 2:
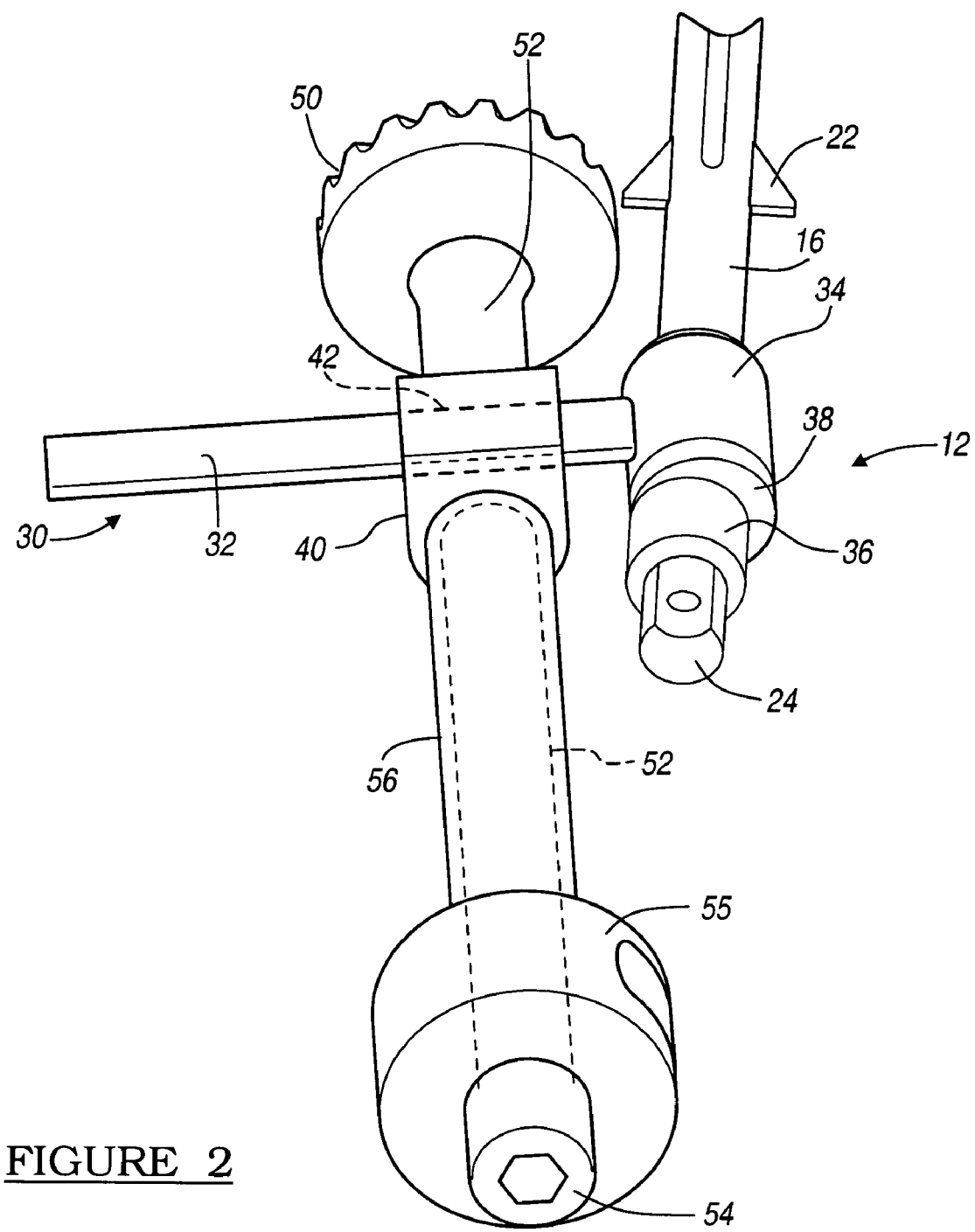
FIG. 2 is a detailed prospective view of the assembly of FIG. 1.
Figure 3:
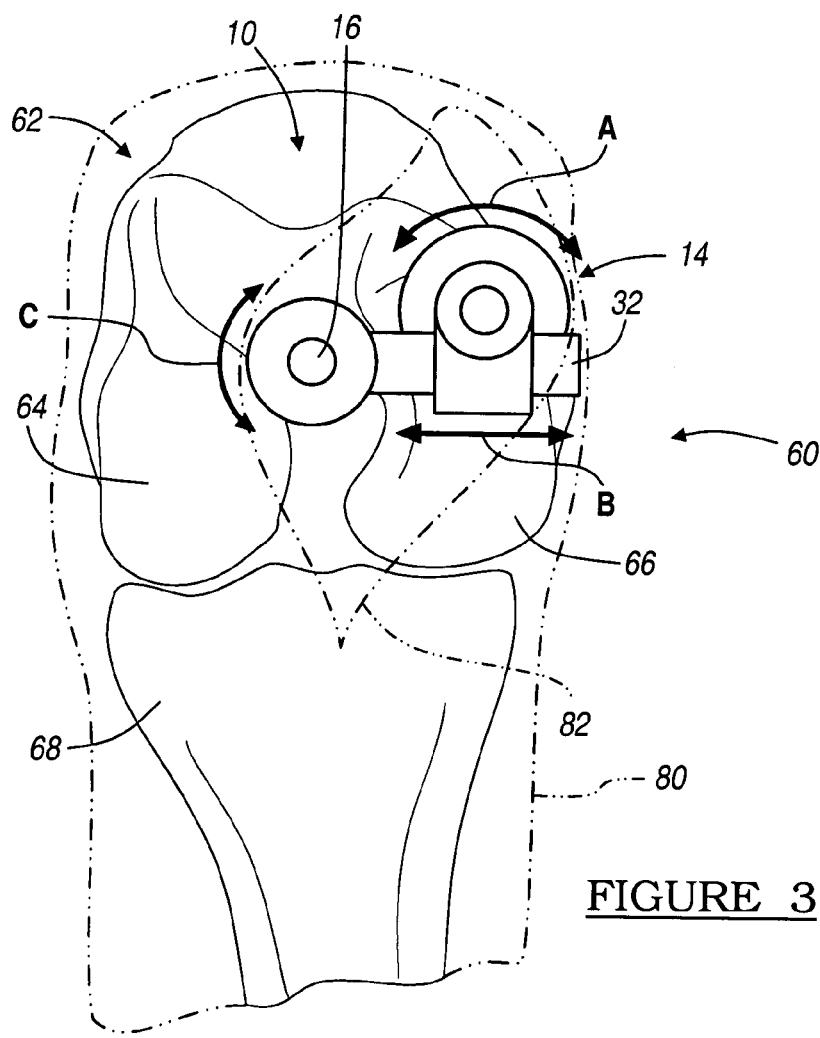
FIG. 3 is a end plan view of the assembly of FIG. 1 implanted.

With continuing reference to FIGS. 1 and 2 and additional reference to FIG. 3, an anatomical portion 60, such as a knee joint, includes a distal femur portion 62 including a first condyle 64 and a second condyle 66. The anatomical portion 60 also includes a tibia 68. Exemplary the orthopedic assembly 10 is connected to the distal femur portion 62 for reaming a portion thereof. As discussed further herein, and briefly illustrated here, the assembly 10 allows for movement of the reamer 14 relative to the distal femoral portion 62 and the condyles 64, 66.

The reamer 14 generally rotates along arrow A. The reamer 14 is able to rotate in any appropriate direction relative to the condyles 64, 66. In an initial position, the reamer 14 is generally positioned relative to the second condyle 66. The reamer 14 may be moved in a direction of arrow B by use of the reamer holding portion 40 relative to the movable arm 32. This allows the reamer 14 to be moved generally medially or laterally relative to the positioning arm 16. Also, the reamer portion 14 may rotate in a direction arrow C around the positioning post 16. For example, the locking nut 36 may be released to allow for rotation of the reamer portion 14 relative to the positioning portion 16. Therefore, the reamer 14 may be rotated from the second condyle 66 to the first condyle 64. Nevertheless, the distal positioning of the reamer 14 may be kept constant such that only a selected portion of the first and/or second condyle 64, 66 is resected and is substantially equivalent for both condyles. It will be understood that only one of the condyles 64, 66 may be resected for selected procedures. For example, only one of the condyles 64, 66 may be replaced.

The orthopedic assembly 10 allows for a selected distal resection of a bone 18, or other appropriate resection. As discussed above, the depth guide 55 is one appropriate method and apparatus to limit the distance of the translation of the reamer 14 and selected reaming amount. Nevertheless, a spacer 70 may also be provided relative to the proximal portion 24 of the positioning rod 16. The spacer 70 may be provided between the rotating member 30 and the bone 18 so that the rotating member 30 is never able to translate closer to the bone than the selected distance of the spacer 70.

In addition or alternative to the spacer 70 is a stop or depth selector 72. The depth selector 72 may be positioned on the reamer 14 or a portion of the reamer 14, such as the reamer shaft 52 to eliminate or select a translation of the reamer head 50 toward the bone portion 18 with the orthopedic assembly 10. Therefore, the reamer 14 may be moved a selected depth relative to the bone 18 such that only a selected portion of the bone 18 is resected.

It will be understood that any or all of depth guide 55, the spacer 70, or the stop 72 may be provided to select a portion of the bone 18 to be resected. It will also be understood that other appropriate methods or portions may be provided on the assembly 10 to limit or select depth of resection. In addition, it will be understood that acuity of the physician or person performing the procedure may be relied upon to limit the amount of resection that occurs.

With reference to FIGS. 3-5A an exemplary method of using the assembly 10 is illustrated. It will be understood that the assembly 10 may be used to resect any appropriate anatomical portion, thus resecting a distal portion of the femur 62 is merely exemplary. The apparatus may be used to resect a selected bone portion and may be used in any appropriate manner, and the following is for clarity of the appended claims and the description only.

With reference to FIG. 3, a skin or soft tissue portion 80 surrounds the anatomical joint 60, generally including the femur 62 and the tibia 68. An incision 82 is generally made in the soft tissue. The incision 82 is generally made substantially parallel to the median plane. Therefore, the incision 82 generally extends substantially superiorly and imperially along the joint portion. The incision 82 can be any appropriate size, but is generally about 1 cm to about 10 cm in length.

Figure 4:
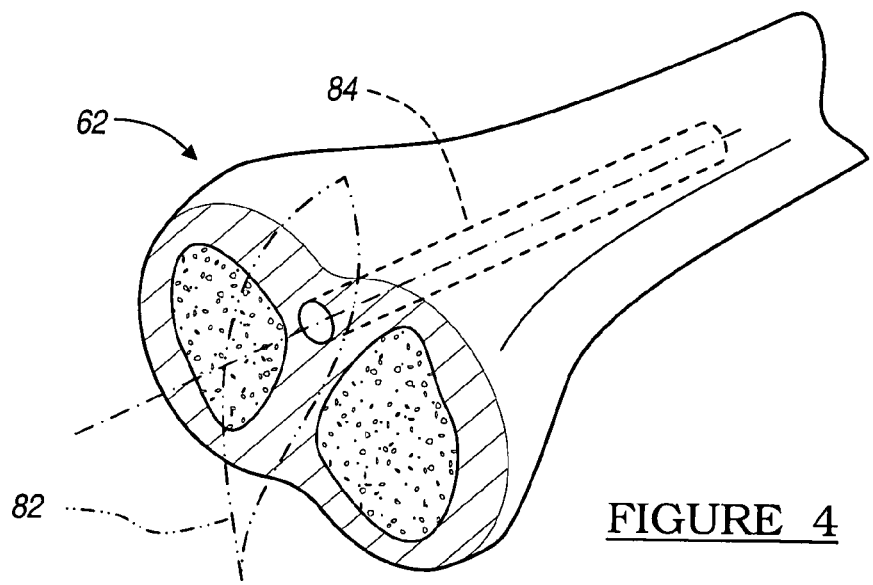
FIG. 4 is a perspective view of a distal end of a femur.

With reference to FIG. 4, after the incision 82 is made, an access or positioning bore 84 is formed in the femur 62. The positioning bore 84 allows for placement of the positioning rod 16 into the femur 62. Generally, the positioning rod 16 is positioned in the femur 62 relative to the positioning bore 84.

It will be understood, however, that the positioning rod 16 may also be self-drilling therefore the bore 84 may not be necessary. Alternatively, the positioning rod 16 may substantially impacted or nailed into the medullary portion of the femur 62 thus also not requiring the positioning bore 84. It will be understood the positioning rod 16 may be positioned in the femur 16 in any appropriate manner. Also, the positioning rod 16 may be only positioned relative to the femur 62.

The positioning rod 16 may be positioned relative to the femur 62 when it is unattached to the rotating member 30 and the reamer 14. That is, the positioning rod 16 can be positioned substantially independently of the other portions of the assembly 10. Nevertheless, it will be understood that the rotating member 30 may be positioned relative to the positioning rod 16 during implantation as may the reamer portion 14 be positioned on the rotating portion 30. Therefore, the modular design of the apparatus 10 allows for various portions of the assembly 10 to be implanted at a selected time. Nevertheless, it will be understood that the selected portions of the apparatus 10 may be formed substantially integrally as a unit and be implanted at a single time.

Figure 5:
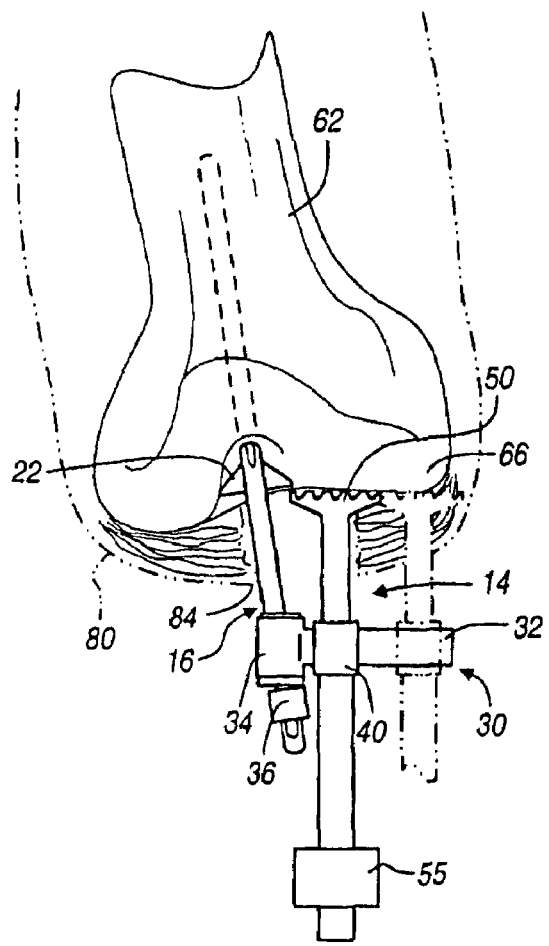
FIG. 5 is a superior plan view of the assembly implanted into a prepared femur.
Figure 5A:
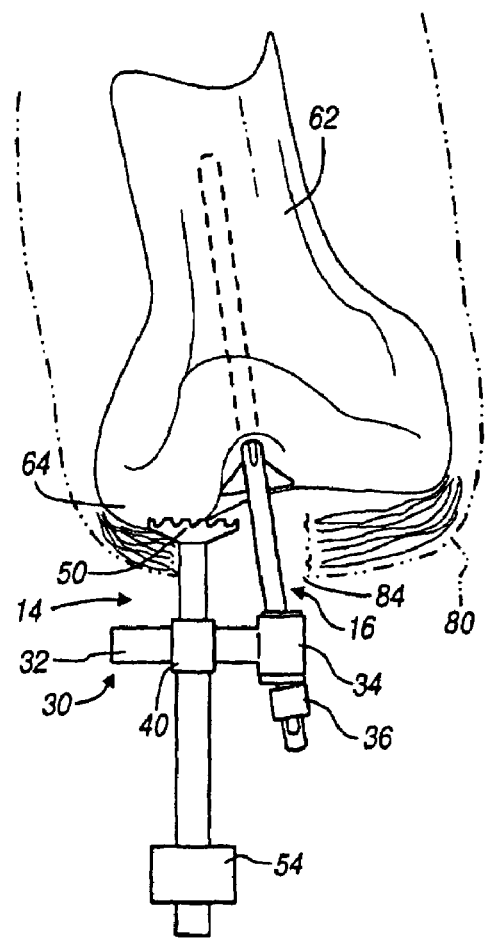
FIG. 5A is an alternative view of FIG. 5.

With reference to FIGS. 3 and 5, after the positioning rod 16 has been positioned into the femur 62, the rotating arm 30 can be positioned relative to the positioning rod 16. The depth guide 55 can be positioned at the selected position on the rod 52 relative to the reamer 14 while it is being implanted. Therefore, the depth guide 55 may interact with the sleeve 56 to substantially select a depth to be reamed. It will be understood that the spacer 70 may alternatively be positioned on the proximal portion of the positioning rod 16 to substantially set the rotating member 30 at a selected distance. Therefore, the translation of the rotating member 30 relative to the positioning rod 16 may be limited. Alternatively, the positioning rod 16 may be substantially free of stop members and the rotating member 30 simply be positioned relative to the positioning rod 16 with appropriate portions, such as the bushing 38 and the locking nut 36. Therefore, the rotating member 30 is positioned relative to the positioning rod 16, at a selected axial distance, but allowed to rotate around the positioning rod 16.

After the rotating member 30 is positioned relative to the positioning rod 16, the reamer 14 is positioned relative to the articulating arm portion 32 of the rotating arm 30. The reamer holding member 40 can be positioned relative to the rotating member 30 by either sliding the reamer holding member 40 over the rotating member 30 or otherwise providing the reamer holding member 40 relative to the rotatable arm 30. It will be understood that the reamer holding member 40 can be provided integrally with the reamer 14 or be a separate component therefrom. Regardless, the reamer 14 is able to rotate relative to the reamer holding member 40 while the reamer holding member 40 holds the reamer 14 in a selected position relative to the rotating arm 30. It will also be understood that the stop 72 may be provided relative to the reamer 14 and the reamer holding member 40 to select an axial translation of the reamer 14. Therefore, only a selected depth of the femur 62 will be resected during the resection procedure.

In the first rotational position of the rotating member 30, a selected portion of the second condyle 66 is resected. The distance or a portion of the second condyle 66 to be resected is selected by the distance which the reamer passes into or towards the femur 62. The depth guide 55 selects or limits the amount that can be resected. Nevertheless, it will be understood that the apparatus may be altered or not include the depth guide 55 to allow for a substantially free resection of the selected bone portion. Also, the reamer 14 is able to translate with the reamer holding member 40 without rotating the rotatable portion 30 relative to the positioning rod 16. Simply, the reamer 14 may be moved without first moving the rotating member 30.

As illustrated in phantom, the reamer 14 may move medially and laterally on and relative to the articulating arm portion 32. Therefore, a substantial or total resection of the condyle 66 is allowed at the selected depth. The reamer 14 may translate relative to the position of the positioning rod 16 and along the articulating arm 32 such that the reamer 14 is substantially the only tool necessary to resect the second condyle 66.

The reamer 14 is able to translate in the direction of arrow B while the reamer rotates in the direction of arrow A. It will be understood, however, that the reamer 14 may be any appropriate tool to resect the second condyle 66. For example, an oscillating saw may also be used to resect the second condyle 66 rather than the rotating reamer 14. Alternatively, the reamer 14 portion may vibrate in a selected or random movement to resect the second condyle 66 without rotating in a substantially circular direction.

The rotating member 30 is also able to rotate about the positioning post 16 in the direction of arrow C. Therefore, the reamer 14 is able to move over substantially the total surface area of the second condyle 66 to resect the selected portion of the second condyle 66. Similarly, with reference to FIG. 5A, the reamer 14 is able to rotate around the positioning post 16 to substantially resect the first condyle 64. The first condyle 64 may be resected substantially equivalently to the second condyle 66 because the positioning rod 16 has not been moved. Therefore, the axial translation of the reamer 14 is so substantially constant and equivalent relative to the positioning rod 16 that is positioned in the femur 62.

The assembly 10 allows the resection of the first condyle 64 to be substantially equivalent to the resection of the second condyle 66. The positioning rod 16 selects a center point around which the rotating member 30 may rotate. Also, the depth guide 55 selects a substantially absolute translation of the reamer 14 relative to the femur 62. Therefore, providing the rotating member 30 at an appropriate length allows the positioning rod 16 to be positioned in substantially one position yet the reamer 14 may move over both the first condyle 64 and the second condyle 66 in a substantially equivalent manner to resect both condyles 64, 66 substantially equivalently. Substantially both condyles 64, 66 of the femur 62 may be resected with the reamer 14. The positioning rod 16 is positioned in the femur 62 to allow for translation of the reamer 14 above the positioning rod 16.

Also, substantially the only portions entering the incision 82 are the positioning rod 16 in the reamer head 50 and a portion of the reamer shaft 54. Therefore, the incision 82 can be kept substantially small and generally about 1 cm to about 10 cm in length. The incision 82 only needs to be large enough to allow access for the positioning rod 16 and the reamer head 50. Therefore, the incision 82 may be kept to a minimum to decrease trauma to the soft tissue and the expected healing time. Nevertheless, it will be understood that the incision 82 may be provided to any appropriate length or size. The incision 82 may be larger to allow for clearer viewing of the condyle 64, 66 or for ease of movement of the reamer head 50. In addition, other small incisions may be provided relative to the femur 62. The other incisions may be arthroscopic incisions to allow use of an arthroscope for increased viewing of the resection area.

The use of the positioning rod 16 and the rotating portion 30 substantially limits the movement of the reamer head 50 to only those that are necessary to resect the condyle 64, 66. As discussed above, the various guides and stops may be provided on the various portions of the assembly 10 such that the reamer 14 is only able to move in the resected areas to resect the selected portions. Therefore, resection of undesired portions of the condyles 64, 66 may be substantially eliminated due to the apparatus 10. Nevertheless, it will be understood that the apparatus 10 may be used for assisting a substantially free resection of the condyle 64, 66. Nevertheless, the apparatus 10 may be used in a substantially blind resection of the condyle 64, 66.

Therefore, it will be understood that the apparatus 10 may be used in a substantially less invasive resection procedure because of the small number of implements that must be positioned through the incision 82. It will also be understood, that the apparatus 10 may be used for resecting any appropriate bone portion and is not limited to resecting the condyles 64, 66 of the femur 62. The assembly 10 may be used to resect any appropriate bone portion through a substantially small incision to limit trauma to the patient.

It will be further understood that the apparatus 10 may be altered slightly and still be within the scope of the above description and the appended claims. For example, the positioning rod 16, as mentioned above, need not necessarily be passed into the bone 18 or the femur 62. Simply, the rod 16 may be positioned relative to the bone 18 or the femur 62 to guide the rotatable member 30. In addition, the articulating or rotating arm 32 may include steps or stops such that the reamer holding member 40 is positioned at a selected point and locked at that point to resect the selected bone portion. This will allow the reamer holding member 40 to be locked at a spot relative to the rotating member 30 and increase the precise resection in a selected pattern, such as a substantial circle. Alternatively, the reamer holding member 40 can be locked on the rotating member 30 and be plunged relative to the femur 62 to resect the selected distance. Thus, even greater control of the resection can be allowed by locking the various members together during the selected reaming times.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A resection assembly to allow resection of a selected bone portion, comprising:
    a positioning rod adapted to be disposed within the selected bone portion;
    a reamer guide portion moveable relative to said positioning rod and adjustably securable in at least a first position and a second position;
    a resecting tool guided by said reamer guide portion such that a selected portion of the selected bone portion is resected, said resecting tool translating in a direction generally along a longitudinal axis of the bone separate from said positioning rod during resection of the selected bone portion;
    a spacer receiving a portion of said positioning rod and disposed between the bone portion and the reamer guide portion during resection and operable to limit said translation of the resecting tool during resection;
    a depth guide assembly including a stop extending from said resecting tool and selectively secured to various positions along said resecting tool and operable to engage said reamer guide portion upon sufficient translation of said resecting tool to thereby limit movement of said resecting tool relative to said positioning rod; and
    wherein said positioning rod and said resecting tool are passed through an incision.

2. The resection assembly of claim 1, wherein only a portion of said positioning rod and a portion of the resecting tool are adapted to pass through the incision.

3. The resection assembly of claim 1, wherein said positioning rod includes:
    a bone engaging section extending along a first axis; and
    a reamer guide engaging section extending along a second axis;
    wherein said reamer guide portion is rotatable about said reamer guide engaging section of said positioning rod.

4. The resection assembly of claim 1, further comprising:
    a reamer engaging member operable to interconnect said reamer guide portion and said resecting tool;
    wherein said reamer guide portion includes an arm portion and a collar portion wherein the collar portion is rotatable about said positioning rod; and
    wherein said reamer engaging member allows for translation along said arm portion of said first guiding member to guide said resecting tool along said arm portion of said first guiding member.

5. The resection assembly of claim 1, wherein said resecting tool includes:
    a milling head adapted to be able to resect a portion of the selected bone portion; and
    a shaft extending from said milling head along a milling axis;
    wherein said milling head is movable along at least said milling axis.

6. The resection assembly of claim 1, wherein said reamer guide portion is fixable relative to said positioning rod at a plurality of positions such that said resecting tool resects a selected position when said reamer guide portion is fixed relative to said positioning rod.

7. The resection assembly of claim 1, wherein the incision is about 1 cm to about 10 cm in length; and
    substantially only said positioning rod and said resecting tool are adapted to extend through the incision.

8. The resection assembly of claim 5, wherein said depth guide assembly includes:

a sleeve positioned relative to said shaft; and
a depth guide member fixable to said shaft;
wherein said depth guide member is able to engage said sleeve to select the axial position of said resecting head to select a depth of the resection of the selected bone portion.

9. An assembly to resect a selected bone portion, comprising:
a positioning member partially disposed within the selected bone portion;
a guiding member rotatably extending from said positioning member that is adjustably securable in at least a first position enabling resection of a first portion of the bone and a second position enabling resection of a second portion of the bone; and
a resecting member guided by said guiding member and rotatable about a resecting axis, said resecting member translating in a direction generally along a longitudinal axis of the bone separate from said positioning member during resection of the selected bone portion;
a depth selection assembly including:
a depth guide operably interconnected with said resecting member to provide an axial depth selection of said resecting member; and
a fixable sleeve operably interconnected with said depth guide, such that said depth guide operably engages said sleeve to select a depth of said resecting member relative to said positioning member;
wherein said resecting member is rotatable around said positioning member to at least one position relative to said positioning member, and wherein said resecting member adjustably positions at a first angle relative to an axis of said positioning member in said first position and at a second angle relative to said axis of said positioning member in said second position and wherein said first position is distinct from said second position and said first angle is distinct from said second angle.

10. The assembly of claim 9 wherein said depth guide threadably translates along a shaft of said resecting member to define said axial depth selection.

11. The assembly of claim 9, wherein at least a portion of said positioning member is adapted to be disposed within the selected bone portion.

12. The assembly of claim 9, further comprising a spacer wherein a first portion of said positioning member is disposed in the medullary portion of the femur and a second portion of said positioning member is received by said spacer.

13. The assembly of claim 9, wherein the positioning member has a width of about 0.5 to about 2.0 cm.

14. The assembly of claim 9, wherein said resecting member includes:
a milling head having a dimension of about 0.5 cm to about 3.0 cm; and
a shaft extending from said milling head having a width of about 0.25 cm to about 2.0 cm.

15. The assembly of claim 9, wherein said guiding member includes:
a first portion operably interconnected to said resecting member; and
a second portion extending from said first portion and operably interconnected to said positioning member to allow said first portion to rotate relative to said positioning member.

16. The assembly of claim 15, further comprising:
a resecting member holder to operably interconnect said resecting member and said second portion of said guiding member;
wherein said resecting member allows for translation of said resecting member along a length of said second portion of said guiding member.

17. The assembly of claim 9, wherein said positioning member and said resecting member operably interact through a substantially less invasive procedure to resect the selected bone portion;
wherein substantially only said positioning member and said resecting member are adapted to engage the selected bone portion.

18. The assembly of claim 9, further comprising:
a second guiding member to operably interconnect said first guiding member and said resecting member;
wherein said second guiding member allows for a selected radial translation of said resecting member relative to said positioning member.

19. A resection assembly to allow resection of a selected bone portion, comprising:
a positioning rod adapted to be disposed within the selected bone portion through an incision formed relative to the selected bone portion;
a reamer guide portion moveable relative to said positioning rod and adjustably securable in at least a first position enabling resection of a first portion of the bone and a second position enabling resection of a second portion of the bone;
a resecting tool movably coupled to said positioning rod and rotatable about a resecting axis, said resecting tool guided by said reamer guide portion such that a selected portion of the selected bone portion is resected;
a spacer adapted to be disposed between the bone portion and said reamer guide portion during resection and operable to limit said translation of said resecting tool during resection; and
a depth guide assembly operable between said reamer guide portion and said resecting tool to select an axial movement of said resecting tool, said depth guide assembly including a depth guide and a sleeve selectively engaged to said resecting tool, wherein said depth guide is movable along said resecting tool to engage said sleeve and limit a depth of cut of said resecting tool;
wherein said positioning rod and said resecting tool are passed through the incision.

20. The resection assembly of claim 19 wherein said resecting tool translates in a direction generally along a longitudinal axis of the bone separate from said positioning rod during resection of the selected bone portion and wherein said resecting tool adjustably positions at a first angle relative to an axis of said positioning member in said first position and a second angle relative to said axis of said positioning member in said second position, wherein said first angle is distinct from said second angle and said first position is distinct from said second position.

21. The resection assembly of claim 19, wherein said resecting tool includes:
a milling head adapted to be able to resect a portion of the selected bone portion; and
a shaft extending from said milling head along a resecting axis;
wherein said milling head is movable along at least said resecting axis.

22. The resection assembly of claim 19, wherein said depth guide assembly includes:
a stop configured to be secured to at least one position on said resecting tool in order to limit axial movement of said resecting tool.

23. The resection assembly of claim 19, wherein said resecting tool includes:
- a resecting head having a dimension of about 0.5 cm to about 3.0 cm; and
- a shaft extending from said resecting head having a width of about 0.25 cm to about 2.0 cm; and
- wherein the positioning member defines a width of about 0.5 to about 2.0 cm.

24. The resection assembly of claim 19 wherein said positioning member extends through a portion of said spacer.

25. The assembly of claim 19 wherein said resecting tool is movably coupled to said positioning member to enable movement separate from said positioning member.

\* \* \* \* \*